United States Patent [19]

Bahl et al.

[11] Patent Number: 5,538,872
[45] Date of Patent: Jul. 23, 1996

[54] METHOD OF PREPARING NUCLEOTIDE PROBES USING A BRIDGING COMPLEMENT

[75] Inventors: Chander Bahl, Flemington, N.J.; Leopoldo Mendoza, Madison, Wis.; Frank J. McMahon, Whitehouse Station, N.J.

[73] Assignee: Ortho Diagnostic Systems, Inc., Raritan, N.J.

[21] Appl. No.: 302,332

[22] Filed: Sep. 8, 1994

Related U.S. Application Data

[63] Continuation of Ser. No. 175,687, Dec. 30, 1993, abandoned, which is a continuation of Ser. No. 827,833, Jan. 28, 1992, abandoned, which is a continuation of Ser. No. 287,431, Dec. 21, 1988, abandoned.

[51] Int. Cl.$^6$ .......................... C12P 19/34; C07H 21/04
[52] U.S. Cl. .................. 435/91.52; 536/23.7; 536/23.72; 536/24.32
[58] Field of Search .......................... 435/5, 6, 91.52; 536/24.3, 25.3, 23.7, 23.72, 24.32

[56] References Cited

U.S. PATENT DOCUMENTS

| | | | |
|---|---|---|---|
| 4,563,419 | 1/1986 | Rarki et al. | 435/6 |
| 4,656,127 | 4/1987 | Mundy | 435/6 |
| 4,699,876 | 10/1987 | Libeskind | 435/5 |
| 4,711,955 | 12/1918 | Ward et al. | 536/29 |
| 4,794,082 | 12/1988 | Sigler | 435/177 |
| 4,797,355 | 1/1989 | Stabinsky | 435/6 |

FOREIGN PATENT DOCUMENTS

| | | |
|---|---|---|
| 0079139 | 5/1983 | European Pat. Off. . |
| 0097373 | 4/1984 | European Pat. Off. . |
| 01117440 | 9/1984 | European Pat. Off. . |
| 0154788 | 9/1985 | European Pat. Off. . |
| 0185494A2 | 6/1986 | European Pat. Off. . |
| 0194545 | 9/1986 | European Pat. Off. . |
| 0237737 | 1/1987 | European Pat. Off. . |
| 0212546 | 3/1987 | European Pat. Off. . |
| 0219695 | 4/1987 | European Pat. Off. . |
| 0224126 | 6/1987 | European Pat. Off. . |
| 0231495 | 8/1987 | European Pat. Off. . |
| 0235726 | 9/1987 | European Pat. Off. . |
| 0285057 | 10/1988 | European Pat. Off. . |
| 0286898 | 10/1988 | European Pat. Off. . |
| 0292128 | 11/1988 | European Pat. Off. . |
| WO84/03285 | 8/1984 | WIPO . |
| WO85/04674 | 10/1985 | WIPO . |
| WO88/01302 | 2/1988 | WIPO . |

OTHER PUBLICATIONS

USB, Molecular Biology Reagents/Protocols 1992, pp. 114–115.

Matthews and Kricka, "Review: Analytical Strategies for the Use of DNA Probes", Analytical Biochemistry 169:1–25 (Feb. 1988).

Sambrook, J. et al., "Molecular Cloning", A Laboratory Manual, Second Edition, Cold Spring Harbor Laboratory Press 1989.

Sanchez–Pescador, R. et al., "Rapid Chemiluminescent Nucleic Acid Assays for Detection of TEM–1–β–Lactamase–Mediated Penicillin Resistance in *Neisseria gonorrhoeae* and Other Bacteria", J. of Clinical Microbiology 26:1934–1938 (1988).

*Primary Examiner*—Mindy Fleisher
*Assistant Examiner*—James Ketter
*Attorney, Agent, or Firm*—Woodcock Washburn Kurtz Mackiewicz & Norris

[57] ABSTRACT

The present invention provides labeled nucleotide probes and a procedure for synthesis of the labeled nucleotide probe by a coupling or joinder of two components of the probe, namely a target recognition sequence moiety and a signal generating moiety, through the use of a bridging complement that holds the two moieties in such a position as to allow formation of a sugar-phosphate chemical linkage between the 3' end of one moiety and the 5' end of the other moiety.

32 Claims, No Drawings

METHOD OF PREPARING NUCLEOTIDE PROBES USING A BRIDGING COMPLEMENT

This is a continuation of application Ser. No. 08/175,687, filed Dec. 30, 1993, now abandoned, which in turn is a continuation of Ser. No. 07/827,833, filed Jan. 28, 1992, now abandoned, which in turn is a continuation of Ser. No. 07/287,431, filed Dec. 21, 1988, now abandoned.

Specific oligonucleotide sequences are very useful tools in detecting complementary nucleotide sequences. The two requirements of the nucleic acid probe are a sequence specific signal and the formation of elements which will convert single hybridization events into multiply detectable events. In current enzymatic methods for preparing labeled probes, radioactive or biotinylated nucleotides are introduced into the probes by the use of polymerizing enzymes like DNA polymerase or terminal transferase. Methods are also available for introducing single enzymes or hapten molecules into DNA chemically, but these singly tagged probes do not generate enough signal, thus lacking the sensitivity needed for detecting complementary sequences in biological samples.

Ward et al. in U.S. Pat. No. 4,711,955, discloses a procedure for labeling nucleotide probes which consists of derivatizing nucleotides with chemical determinants. The derivatized nucleotides are then enzymatically polymerized. Thus, these analogs function as substrates for nucleic acid polymerases. For this purpose, it is crucial that the chemical determinants not be placed on ring positions that sterically, or otherwise, interfere with normal Watson Crick hydrogen bonding potential of the bases.

SUMMARY OF THE INVENTION

The present invention provides an alternative to the synthesis of nucleic acid probes known to the art. The procedure produces a labeled nucleotide probe having a first "target recognition moiety" and a second "signal generating moiety". Each moiety comprises a 3' and a 5' terminus, the two moieties being attached to one another in a 3'–5' configuration. The procedure comprises the steps of:

a) providing a first "target recognition moiety" having a first specific end sequence of at least about 4 nucleotide bases, b) providing a second "signal-generating moiety" having multiple label attached thereto and also having a second specific end sequence of at least about 4 nucleotide bases, c) providing a third "bridging complement" comprising a nucleotide sequence of about 8–25 nucleotides, at least about 4 of said nucleotides in said bridging complement being capable of hybridizing to said specific end sequence of said "target recognition moiety" and at least about 4 other nucleotides in said bridging complement capable of hybridizing to the specific end sequence of said "signal-generating moiety";

d) allowing, under appropriate hybridization conditions, hybridization of said bridging complement to the first specific end sequence of said "target recognition moiety" and the second specific end sequence of said "signal generating moiety" to form a hybridized complex of all three;

wherein the 3' terminus of one of said moieties is aligned with the 5' terminus of the other, said 3' terminus and said 5' terminus being positioned relative to one another in such a manner as to allow formation of a 3'–5' sugar-phosphate link between the first and second moieties; and e) contacting said complex with a DNA ligating means in such an amount and for such a period of time as is effective to allow formation of said sugar-phosphate chemical attachment between said 3' end and said 5' end of said first and second moieties, to produce a nucleotide probe comprising said "target recognition moiety" and said "signal generating moiety" chemically attached to one another.

After formation of this sugar-phosphate attachment, the method of the invention may also comprise step (f), which comprises the contacting of said complex having said moieties chemically attached with an enzyme capable of removing said bridging complement from said complex.

The present invention also provides labeled nucleotide probes formed from this chemical joinder of the two components and diagnostic and research reagents containing said probes.

As used herein, the term "nucleotide probe" means a labeled nucleotide sequence having as part of that sequence, a moiety that can hybridize, at least in part, to an analyte nucleotide sequence, and can be useful to detect, monitor, localize, isolate and the like, said analyte sequence. The term should be interpreted broadly to include oligonucleotides, homopolynucleotides, polynucleotides and the like.

As used herein, it is understood that "hybridization" refers to complementary base pair binding to all or a portion of a target nucleic acid sequence, i.e: the probes must contain at least some complementarity. It should be understood that this binding does not have to be perfectly matched. There may, in fact, be unpaired regions, resulting in interior loops, bulge loops, hairpin loops, cruciform binding, or any other mismatched regions. Hybridization need only occur to the extent necessary to allow detection of the target.

As used herein, the term "target recognition moiety" means that part of the probe that will hybridize or bind to sample analyte. The target recognition moiety comprises a nucleotide sequence and can take on any suitable configuration for binding to said analyte, whether that be a specific sequence of nucleotide bases, a homopolynucleotide sequence, or the like.

As used herein, "signal generating moiety" means that part of the probe that can generate a signal through a radioactive label, enzymatic label, chemical label, immunogenic label, and the like.

As used herein, "target analyte sequence" refers to all or a portion of the nucleic acid contained in or relating to biological matter that may be found in a biological, physiological, environmental sample or the like.

As used herein, "5' end" and "3' end" should be construed as the meaning generally accepted in the art, namely, the terminal nucleotide at one end of a nucleotide sequence has a free 5' or 3' group, wherein the ester oxygen of the phosphodiester linkage is free to join to either the fifth or third carbon atom respectively of a pentose.

DETAILED DESCRIPTION OF THE INVENTION

The present invention provides a procedure for synthesis of a labeled nucleotide probe by a coupling or joinder of the two components of the probe, namely the target recognition sequence moiety and the signal generating moiety, through the use of a bridging complement that holds the two moieties in such a position as to allow formation of a sugar-phosphate chemical linkage between the 3' end of one moiety and the 5' end of the other.

To prepare a labeled probe using the method of the invention, a first binding nucleotide sequence, the target recognition sequence moiety, is provided by any suitable means. For example, this moiety may be isolated from the genomic DNA or RNA of an organism it is desired to detect, it may be recombinantly produced, or it may be chemically synthesized by standard oligonucleotide synthesis procedures. A good description of such suitable procedures for the latter may be found in Methods in Enzymology, Volume 154, pages 221–328, Academic Press N.J. 1987, Ray Wu and L. Grossman, editors.

Any configuration of nitrogenous bases, including adenine, guanine, cytosine, thymine, uracil, or methylcytosine, are contemplated to form the nucleotide sequence of this target recognition sequence moiety as long as the moiety is capable of binding, at least to some extent, with at least a portion of the nucleic acid of an analyte. The binding event itself is any complementary base pair binding suitable to allow detection of the target analyte.

The length of the target recognition sequence moiety may vary widely, ranging from several hundred bases to about 5 bases, and preferably about 5–75, more preferably about 5–60, and most preferably about 15–50 bases. It should be appreciated that the length of this binding moiety will be governed to some extent by the binding characteristics of the analyte sequence itself, and may be optimized by the routineer in the art.

The preferred sequence lengths range under about 100 bases long and preferably about 15–50 bases long, as it has been found that this length simply affords ease of use. This is generally due to the phenomenon that sequences in the range of 15 to 50 are easy to synthesize conveniently, and cost effectively, and have enough hydrogen bonds to give stable double-stranded structure to survive various manipulation and treatments. Sequences of greater than about 100 bases can pose difficulty during use in that they may be more difficult to synthesize, may be less cost effective, and may tend to increase intramolecular secondary structures. Those skilled in the art will understand that beyond a certain length, very little additional stability is imparted to the hybrids by virtue of increasing the length of sequences.

It should be appreciated that in some instances it may be desirable to incorporate derivatives or other chemical moieties at various positions in this target recognition sequence, for a variety of reasons such as to serve as reporter molecules directly or indirectly. Any such derivatives are within the contemplation of the invention, as long as the addition of such chemical derivatives to various positions in the target recognition sequence does not interfere substantially with binding of this moiety to analyte.

When a phosphate group is not positioned on one or both terminal nucleotide residues of the target recognition moiety, a phosphate residue is added to the oligomer in a conventional manner such as by the use of "5 Phosphate-on" cyanoethyl phosphoramidiite, polynucleotide kinase, and the like, to provide a phosphate moiety for the sugar-phosphate linkage. The target recognition moiety may then be purified using well-known techniques such as column chromatography, gel electrophoresis, and the like.

The second moiety of the probes of the invention, the signal generating moiety, is provided by any suitable means, such as those described for the target recognition moiety. The signal generating moiety of the probe comprises any nucleotide sequence that is capable of containing multiple detectable label, and is further capable of chemical linkage to the target recognition moiety by a 3'–5' sugar-phosphate bond. The nucleotides may vary widely in their specific sequence, as long as they contain enough label to be capable of signaling the binding of the target recognition moiety of the probe to analyte, and hence must contain multiple label. By multiple label is meant that the signal moiety has at least two (2) signal generating elements attached to it, and preferably 5–15, most preferably 8–10. The advantage afforded by the signal moiety as described herein is that it enables the user to provide multiple labels at defined places, and also to label this portion prior to its chemical attachment to the target recognition moiety.

The signal generating moiety may be obtained commercially or prepared from any appropriate source, including denatured single-stranded DNA from natural sources, RNA from natural sources, or chemical synthesis of oligonucleotides, polynucleotides, homopolynucleotides, or homooligonucleotides. This sequence varies in length in a manner commensurate with the signal amplification required and the amount of label it is desired to attach. However, lengths of about 50 to 200 nucleotide bases have been found to be particularly useful due to the fact that this number of nucleotides have the potential for carrying enough label for detection, but do not unduly effect the rate of hybridization, and are easy and economical to synthesize.

The labeling of the nucleotide sequence in the signal generating moiety may take on many forms, including conventional radioisotopic labeling, chemical labeling, immunogenic labeling, or a label with light scattering effect, and the like. Thus, the label of the signal generating moiety may comprise a radiolabel (e.g. $^{14}C$, $^{32}P$, $^{3}H$, and the like), an enzyme (e.g., peroxidase, alkaline or acid phosphatase, and the like), a bacterial label, a fluorescent label (a fluorophore), an antibody (which may be used in a double antibody system), an antigen (to be used with a labeled antibody), a small molecule such as a hapten like biotin (to be used with an avidin, streptavidin, or antibiotin system), a hapten such as fluorescein to be used with an anti-fluorescein antibody, a latex particle (to be used in a buoyancy or latex agglutination system), an electron dense compound such as ferritin (to be used with electron microscopy), or a metal, such as a light scattering particle such as colloidal gold, or a catalyst, or a dye, or any combinations or permutations thereof.

For example, if the label of the signal generating moiety is an antigen, a signal can be generated by complexing said antigen with an antibody/enzyme conjugate, followed by addition of enzyme substrate. If the label of the signal generating moiety is an antibody, signal can be generated by complexing anti-antibody or an $F_c$ binding protein such as Protein A therewith, which second antibody or Protein A have been conjugated to an enzyme.

For reasons of ease and safety in the handling of the probe, it is preferred that the signal generating moiety be chemically labeled, especially immunogenically or enzymatically. In more preferred embodiments, the chemical label of choice is a hapten, such as biotin, iminobiotin, fluorescein, and the like. These are preferred at the present time due to ease of synthesis and availability of high specific activity secondary reagents. Certain of the nucleotide bases contained in the signal generating moiety may be modified to introduce amine or other derivatizable groups, using conventional techniques, prior to attachment of the chemical label.

By way of illustration, in one preferred embodiment, the signal generating moiety is based on the biotin/streptavidin system. This system can be incorporated into the signal generating moiety by a variety of means. For example, a polynucleotide portion of the signal generating moiety can be covalently attached to biotin via a cytochrome c bridge (Manning et al, Biochemistry, 16:1364–1370 (1977), Manning et al, Chromosoma, 53:107–117 (1975), Sodia, A., Nucleic Acids Research, 5: 385–401 (1978)), or the biotin can be covalently incorporated into specific nucleotide residues (Langer, P. R., Proceedings of one National Academy of Sciences, USA, 78:6633–6637 (1981), or the biotin can be attached to a polynucleotide by means of a diamine (e.g., pentane diamine) bridge (Broker, T. R., et al, Nucleic Acids Research 5: 363–384 (1978)). Interaction of the biotin molecules in the signal generating moiety with avidin, streptavidin or antibiotin antibodies is then carried out, wherein the avidin, streptavidin or the antibodies are conjugated to such signalling components as latex particles (Sodia, A., et al, supra or Manning, et al Chromosoma, supra), ferritin (Broker, supra), a fluorogen such as fluorescein, an enzyme, secondary antibodies, magnetic particles, or the like.

It should also be noted that the function of the signal generating moiety is to signal the presence of binding to analyte nucleotide sequence. Hence, it is undesirable for nucleotides within this signal moiety to hybridize to analyte or, for that matter, any other bases that may be present in a sample under analysis. It is therefore preferable to substitute the 4 exocyclic amino groups on cytosine residues with a hapten such as biotin, immunobiotin, fluorescein, or the like, to prevent this base's normal hybridization function, thereby ensuring that the hybridization of the probe will be through the target recognition moiety and not via the signal generating moiety. After formation, the signal generating moiety may be purified using conventional techniques.

The third moiety, a bridging complement, is provided in any suitable fashion. In preferred embodiments, the bridging complement is an oligomer of about 8 to about 25 nucleotides synthesized using conventional DNA synthesis techniques. Of course, this presupposes that the terminal sequence of either the 5' or 3' end of both the target recognition moiety, and the signal generating moiety, is substantially known. In many cases, the signal generating moiety will be a homopolynucleotide. Thus, the bridging complement need only contain at least four complementary homopolynucleotide bases. As for the target recognition moiety, its sequence is complementary, at least in part, to target analyte sequence. Hence, sequencing information from at least one of the ends of this moiety would have to be known in order to generate a corresponding bridging complement. Alternatively, if the target recognition moiety is chemically synthesized, a homonucleotide sequence may be generated on one or both ends. A corresponding complementary bridging moiety may then be easily generated for the third binding moiety. Thus, a bridging complement may be synthesized that contains at least four nucleotides complementary to the end sequence of both the signal generating moiety, and the target recognition moiety. In preferred embodiments, each of the complementary nucleotide portions of this bridging complement is separated from each other by no more than one nucleotide base. This will ensure that the end sequence of the target recognition moiety and the end sequence of the signal generating moiety, when brought into alignment with one another, will be close enough to one another to allow the formation of a sugar-phosphate bond.

In the preferred embodiments, after formation of the bridging complement, it is purified in a manner that enables an accurate estimate of its concentration. Knowledge of an accurate concentration of the bridging complement is useful in determining the stoichiometry of the three reactants to be annealed. It should be appreciated that a better quality probe may thus be obtained, without extensive purification after formation. Purification techniques suitable for this purpose include reversed phase high pressure liquid chromatography, gel electrophoresis, and the like, as these procedures are known to be sensitive in this regard.

The three moieties as described above are allowed to anneal, forming a complex wherein the bridging complement holds the target recognition moiety and the signal-generating moiety in such a position as to allow formation of a sugar-phosphate chemical linkage between the 3' end of one of the moieties, and the 5' end of the other. This annealing process may be carried out using conventional hybridization techniques. For example, the three moieties may be mixed at elevated temperatures to melt the intramolecular secondary structures. Typical cooling processes may then be employed to ensure that the most stable hybrid complexes are formed. A sugar phosphate bond may be induced to join the target recognition moiety to the signal generating moiety using a suitable DNA litigating means. Any conventional means may be used for this purpose, such as, for example, chemical means of ligation (Z. A. Shabarova, M. S. Ivanovskaya, and M. G. Isaguliants, FEBS Letters, Vol. 154, Number 2, April 1983); photoligation means "DNA Assay Using Template-Directed Photoligation", San Diego Section of the American Association of Chemical Chemistry-AMOCO Technology Company, P.0. Box 400, Naperville, Ill. 60566; or enzymes specific for this purpose. Of the latter may be mentioned enzymes such as the ligases; for example: $T_4$ DNA ligase, $E.\ coli$ ligase, and the like.

If it is desired to remove the bridging complement prior to use of the labeled nucleotide probe in a hybridization assay, the complex may be subjected to alkaline conditions, elevated temperatures, and other like techniques to denature the bridging complement from the complex. The disassociated bridging complement is then removed by any suitable purification techniques, such as chromatography methods and the like. It should be appreciated, however, that the bridging complement does not necessarily have to be expressly removed prior to the use of the probe in a hybridization assay. Stringent hybridization conditions (discussed infra) often suffice to effect removal of the bridging complement without requiring additional steps expressly for this purpose.

The nucleotide probe constructed as above may be provided as a liquid reagent by being retained in a solution conducive to hybridization reactions, such as water, aqueous buffers, buffers containing formamide, and the like. In the preferred embodiments, such liquid reagent may contain suitable hybridization enhancers, detergents, carrier DNA, and compounds to increase the specificity, such as formamide. Such liquid reagent may comprise one or more nucleotide probes prepared as described herein, in any combination, as the probe portion of the reagent. In the liquid reagent form, the shelf-life generally ranges over one year.

Alternatively, the probe may be lyophilized, and thus provided in dry reagent form. Prior to use, the lyophilized reagent is reconstituted with a suitable solution as described above, optionally containing one or more of the previously described components.

The use of the hybridization probes prepared as described by this invention in hybridization assays assumes the prior selection of a polynucleotide target analyte sequence. In many embodiments, detection of a particular analyte sequence will be desired because the particular sequence of purina and pyrimidine bases on the target polynucleotide is known or thought to be characteristic of a mutated or normal gene of an organism, and because the presence or absence of this particular mutated or normal gene can be correlated with the presence or absence of an infectious agent, carcinogen, disease state, or some other genetic trait.

The target analyte sequence may be present in various media, most often in a biological, physiological, or environmental specimen. It is preferred in some cases to subject the specimen containing the target analyte sequence to a variety of extraction, purification, and isolation protocols before conducting analysis according to the methods of this invention. Measures such as these are desirable to rid the sample of substances that might interfere with binding of the analyte to the hybridization probe. Examples of such protocols may be found in the second chapter of *Nucleic Acid Hybridization*, ed. B. Hames & S. Higgins, IRL Press, Washington, D.C. (985), and in standard textbooks.

It is also within the contemplation of the present invention that synthetic homo- or hereto-poly-nucleotides can be prepared in the laboratory to serve as the target analyte sequence despite their abiological origins, as such synthetic polynucleotides are often desirable for research purposes and the like.

The use of the probes prepared as described herein is not limited to any specific means of hybridization of the probes to the target nucleic acid in a biological specimen, to detect the target sequence. Several hybridization assay techniques are known to the art and include, for example, dot blot hybridization, Southern blotting; sandwich hybridization assays such as those described by Ranki, et al., in U.S. Pat. Nos. 4,563,415 and 4,486,539; sandwich hybridization on beads as described by Hansen, et al. in European Patent Application No. 84306513.7; displacement hybridization techniques such as those described in WO 87/03911; capture techniques wherein the nucleic acid probes is first immobilized onto a solid support and then contacted with sample; in situ hybridization such as those cited or described by Ploeg, Folia Histochemica et Cytobiologica, Vol. 24 (1986) No. 3, pp 189–194; and the like.

It is preferred in most cases that the target analyte sequence be in a single-stranded form to facilitate hybridization to the target recognition moiety of the probe nucleotide sequence. Sample containing target analyte sequence must often be treated to convert any target analyte to single-stranded form. This conversion to single-stranded form may be accomplished by a variety of ways conventional to the art. For example, the denaturation of duplex nucleic acids can be accomplished thermally, chemically or in other conventional ways. The denaturation process will depend upon the pH, ionic strength, temperature, and other properties of the ambient medium (e.g., presence of urea, formamide, glyoxal, methyl mercury hydroxide or other agents), as well as upon the base composition (i.e., the GC/AT ratio), sequence, and length of the duplex nucleic acid. Reviews of various methods of denaturation may be found in standard textbooks, and in J. Marmur, C. Schildkraut and P. Doty in *Molecular Basis of Neoplasia*, Univ. of Texas Press, Austin, Tex., 1962.

In some hybridization procedures it may be appropriate to mix the sample containing target analyte with a "second solution" so as to produce a medium known to support rehybridization of complementary single-stranded nucleic acids. The second solution may be aqueous or nonaqueous or a mixture of both. Certain inorganic or organic additives known to affect rehybridization of complementary single-stranded nucleic acids may be added to enhance the rate of hybridization and/or to increase the equilibrium extent of rehybridization (i.e., stability of the rehybridized form). Of the inorganic additives may be mentioned sodium citrate and sodium chloride; of the organic compounds may be mentioned such compounds as formamide. Other useful additives are polyethylene glycol, dextran sulfate, sodium dodecyl sulfate and casein.

By way of illustration only, one hybridization method comprises contacting probe with a liquid sample under conditions which the analyte target nucleotide sequence, if present, can hybridize in whole or in part to a complementary region contained in the target recognition moiety of the probe nucleotide. This contacting step may be effectuated in a variety of ways, and under varying conditions of "stringency". A review of factors which affect rehybridization (reassociation) processes is available in *Nucleic Acid Hybridization*, ed. B. Hames and S. Higgins, IRL Press, Washington, D.C. (1985). The factors include conditions of temperature, pH, salt concentration and solvent medium, in addition to factors which reflect the length, complexity, and degree of complementarity of the probe and analyte target polynucleotides. The contact period may vary depending on the length of time necessary to effect hybridization to the desired extent, which is dependent in part on the length of the binding region in the target recognition moiety as well as the reaction conditions.

The nucleotide probe, with any bound complementary target analyte sequence is separated from the biological sample after the desired hybridization has taken place. This separation may be accomplished by any suitable procedure including, but not limited to chromatography (column, gel, etc.), filtration, electrophoresis (including electroelution) and the like. It may be further desirable to incorporate a rinsing step or any other appropriate separation step, to ensure that unbound material is fully separated from rehybridized material which has bound to the probe.

Once the hybridization event has taken place and the bound material is separated from unbound, detection of the label on the signal generating moiety is undertaken by assaying the bound material, unbound material, or both. If the label is a radioactive one, direct detection can be accomplished through conventional radioisotopic quantitation techniques. If the label is a chemical one, as for example, biotin, indirect detection takes place.

1. Preparation of Nucleic Acid Probe for the Detection of *Neisseria gonorrhea* a) The target recognition moiety, a Neisseria gonorrhea nucleotide sequence specific oligomer, 50 nucleotide bases in length, was synthesized by typical phosphoramidite chemistry on a DNA synthesizer. After the synthesis, a phosphate residue was chemically added with the synthesizer, using "5 Phosphate on" cyanoethyl phosphoramidiite, after which the oligomer was deblocked to remove the protecting groups. Alternatively, the phosphate group was added by the action of polynucleotide kinase (after deblocking). The oligomer was purified after the synthesis over a Sephadex G-25 column. This oligomer constituted the target recognition moiety.

b) The signal generating moiety oligomer was synthesized on a DNA synthesizer, and in some cases, the capping step after each coupling was eliminated. The oligomer was 50–200 bases in length; 20–100% of the bases being cytosine residues (C). At the 5' end there was a stretch of 8 thymidine residues. After deblocking and then desalting over Sephadex G-25, the oligomer was lyophilized and the exocyclic amino groups of the C's were transaminated by adding 2 mls of transamination mix to the dried oligomer. The mixture was then shaken at room temperature for 24–72 hours. The transamination mix was made up as follows: 5.67 g of hexanediamine dihydrochloride was mixed with 0.231 g of morpholinoethane sulfonic acid in 500 microliters of concentrated sodium hydroxide in a 50 ml screw capped tube. The volume was brought to 9.5 mls with warm water and the mixture was shaken until it was substantially dissolved. 1 g of sodium metabisulfite was added and dissolved, and the pH was adjusted to 6.0–6.2. After the reaction proceeded for 24–72 hours, the pH was brought up to 8.5 for two hours, and then reduced to 7 for 30 minutes. The product was then purified over a 1×40 cm Sephadex G-50 column.

c) The transaminated signal generating moiety oligomer was labeled with hapten, either biotin or fluoroscein isothiocyanate (FITC) either before or after the ligation (annealing process described herein) to the target recognition moiety oligomer. In either case, the biotin (NHS-LC-biotin) or FITC was dissolved in dimethylformamide and mixed with an equal volume of the transaminated oligomer dissolved in 0.1M sodium bicarbonate, pH 9.0, so that the ratio of hapten to amino groups was at least 2. The mixture was allowed to stand at room temperature for 16 hours. Unreacted hapten was removed by Sephadex G-25 chromatography. Alternatively, the excess FITC was removed by one or two butanol extractions followed by Sephadex G-25 chromatography. In both cases, the purified oligomer was lyophilized and redissolved in water.

d) The bridging complement oligomer, a 14–16 met consisting of 8A residues at the 3' end and 6–8 residues at the 5' end that were homologous to the first 6–8 residues of the target recognition moiety, was synthesized with the terminal trityl group left on, and purified by reversed phase HPLC. This oligomer was purified in this way in order to obtain an accurate estimate of the concentration of the oligomer.

e) The three oligomers as described above were annealed as follows: 1 nmole of each of the oligomers was mixed in 50 mM tris-HCl, pH7.5, 10mM MgCl$_2$ (final concentration) and brought to 70° C. The temperature was allowed to fall to 50° C. over about 1 hour and the reaction mixture was transferred to a 37° C. water bath. The bath was turned off and the temperature was allowed to fall to about 25° C. It was then transferred to a 12° C. water bath. After 1 hour at 12° C., the ligation was started by adding cold dithiothreitol (10 mM) and ATP(1 mM), (final concentrations), and 40 units of T4 DNA ligase. The reaction was allowed to proceed for 16 hours at 12° C. EDTA was then added to a final concentration of 20 mM and the reaction mixture was heated to 95° C. for 10 minutes.

f) In some cases, after the ligation reaction, the unreacted target recognition moiety oligomer was removed by passing the sample over a Sephacryl-200 column (2×100 cm in size).

g) Characterization of the Product: The labelled probe was characterized in two ways. The first was by polyacrylamide gel electrophoresis, where an increase in the molecular weight of the product was noted as evidence that the ligation was successful. Secondly, the product was shown to be functional in detecting *Neisseria gonorrhea*. The hybridization assay was carried out as follows:

h) *Neisseria gonorrhoeae* cultures were grown on a selective enriched media such as straight, Tayer Martin (TM), modified Thayer Martin (MTM), New York City (NYC) or Martin Lewis to insure the isolation of pathogenic Neisseria species. Inoculated media were incubated at 35°–36° C. in a humid 3–7% carbon-dioxide atmosphere until bacterial growth was evident (16–24 hrs.). Cultures were inspected visually for colony morphology. Isolates were not older than 96 hrs. (4 days). Suspect organisms were lifted from the plates by gently touching the bacterial colony with the flattened end of an applicator stick. The applicator was then used to dab the bacteria onto a test dot affixed to a test paddle. A single 1 mm colony was sufficient to perform this assay, so the test dot would not be overloaded. The bacteria was applied as evenly as possible and damage to the test dot, by scratching, tearing or excessive pressure was avoided. The innoculated test paddle was then placed on a heat block at 37° C. A small bead (approximately 10 micorliters) of lysis reagent (0.5M alkali containing detergent) was added directly onto the test dot. The paddle was incubated for one minute at 37° C. The paddle was then removed from the heat block and placed in a neutralizing reagent (0.5M Tris/CHl containing detergent) for one minute. The paddle was then returned directly to the heat block without delay, excess reagent was blotted off with absorbent paper using direct pressure.

A small bead (approximately 10 microliters) of the probe reagent (biotinylated or FITC-conjugated *N. gonorrhoeae* specific probe and buffer containing 50% formamide, 10% hybridization enhancer, Triton X-100 and carrier DNA) was placed directly onto the test dot. The paddle was incubated for one minute at 37° C. and blotted as before. Then, a small bead (approximately 10 microliters) of conjugate reagent (streptavidin-horseradish peroxidase complex or anti-FITC antibody, containing 1% carrier proteins and stabilizers and preservative, 0.15% thimerosal) was added directly onto the test dot and incubated for one minute at 37° C. The paddle was removed from the heat block and excess reagent was tapped off. The paddle was then placed in a wash reagent to wash off excess probe and enzyme conjugate. The wash reagent contained a reducing agent and detergent. The paddle was soaked for two minutes and agitated intermittently. The paddle was returned to the heat block and blotted as before.

In the case of the biotinylated probes, a small bead (approximately 10 microliters) of substrate solution (buffer containing hydrogen peroxide and TMB) was added directly to the test dot. The paddle was incubated for one minute at 37° C. The paddle was removed from the heat block and placed in a stop reagent (1% sodium azide) for approximately 10 seconds. The paddle was then removed, blotted and visually read to confirm the presence of *N. gonorrhoea*. A positive test for *N. gonorrhoeae* produced a distinctive blue signal. The negative result ranged from no discernible signal to a faint blue background coloration. The FITC-labeled probes were detected using conventional techniques. The biotin or FITC was detected only where the probe had hybridized to DNA from *N. gonorrhea*, indicating that the target recognition moiety was covalently attached to the signal-generating oligomer.

EXAMPLES

2. Preparation of Nucleic Acid Probe for the Detection of Salmonella a) A labeled oligonucleotide probe for the detection of Salmonella was constructed as follows. A 40 mer corresponding to a portion of Salmonella nucleotide sequence was synthesized on a DNA Synthesizer, and the 5' end of this oligonucleotide was phosphorylated chemically. This constitutes the target recognition moiety.

b) For the signal generating moiety, a 100 mer polynucleotide with 8 thymidine residues at its 3' end was generated;

the remaining nucleotides were cytosines. This polynucleotide was treated with hexyldiamine in the presence of sodium bisulfite to transaminate the exocyclic amino with a hexyldiamino group (see Hyatsu, H. Progress in Nucleic Acid Research and Molecular Biology, Vol. 16 pp. 75–115 (1976)). The polynucleotide could then be treated with a variety of primary amine reactive reagents to introduce haptens into this DNA. In this particular case, fluorescein isothicynate was used to introduce fluorescein residues into the detection part.

c) For the bridging complement, a 16 mer which had 8 adenine residues at its 5' end and 8 nucleotides at 3' end complementary to the first 8 nucleotides at the 5' end of the target recognition moiety, was generated.

d) The three components were mixed in approximately equal amounts, and approximately 40 units of T4 DNA ligase was added to covalently join the target recognition sequence moiety to the signal generating moiety.

e) After purification by conventional gel filteration methods, the probe was tested for its Salmonella detection efficacy in a hybridization assay following the assay steps described in Example 1 above. Fluorescein was detected only when the probe hybridized to its appropriate target.

What is claimed is:

1. A method for the synthesis of a labeled nucleotide probe for detecting a target analyte sequence having a target recognition moiety and a signal generating moiety, each moiety having a 3' terminus and a 5' terminus, said method comprising the steps of:
   a) providing a target recognition moiety having a specific end sequence of at least about 4 nucleotide bases;
   b) providing a signal generating moiety that does not hybridize to the molecule which comprises said target analyte sequence, said signal generating moiety having multiple labels attached thereto and having a specific end sequence of at least about 4 nucleotide bases;
   c) providing a bridging complement comprising a nucleotide sequence of about 8–25 nucleotides, at least about 4 of said nucleotides in said bridging complement being capable of hybridizing to said specific end sequence of said target recognition moiety and at least about 4 other nucleotides in said bridging complement capable of hybridizing to said specific end sequence of said signal generating moiety;
   d) allowing, under appropriate hybridization conditions, hybridization of said bridging complement to at least part of said specific end sequence of said target recognition moiety and at least part of said specific end sequence of said signal generating moiety to form a hybridized complex of all three;
   wherein the 3' terminus of one of said moieties is aligned with the 5' terminus of the other, said 3' terminus and said 5' terminus being positioned relative to one another in such a manner as to allow formation of a 3'–5' sugar-phosphate link between the target recognition and signal generating moieties; and
   e) forming said 3'–5' sugar-phosphate link between said 3' terminus and said 5' terminus of said target recognition and signal generating moieties, to produce a nucleotide probe comprising said target recognition moiety and said signal generating moiety covalently attached to one another.

2. The method of claim 1 further comprising step (f) contacting said complex with an enzyme capable of removing said bridging complement from said complex.

3. The method of claim 1 wherein said nucleotide probe is labeled with a hapten.

4. The method of claim 3 wherein said hapten is biotin.

5. The method of claim 3 wherein said hapten is fluorescein.

6. The method of claim 1 wherein said bridging complement comprises about 14 nucleotide bases.

7. The method of claim 1 wherein the target recognition moiety is a DNA sequence.

8. The method of claim 1 wherein the target recognition moiety is a RNA sequence.

9. The method of claim 1 wherein the target recognition moiety is an oligonucleotide.

10. The method of claim 1 wherein the target recognition moiety is the sequence from a microorganism.

11. The method of claim 10 wherein the microorganism is a virus.

12. The method of claim 10 wherein the microorganism is a bacterium.

13. The method of claim 12 wherein the bacterium is a Neisseria.

14. The method of claim 12 wherein the bacterium is a Salmonella.

15. The method of claim 12 wherein the bacterium is a Shigella.

16. The method of claim 10 wherein the microorganism is Mycoplasma.

17. The method of claim 1 wherein the signal generating moiety is a polynucleotide.

18. The method of claim 1 wherein the signal generating moiety is nucleic acid.

19. The method of claim 18 wherein the nucleic acid is DNA.

20. The method of claim 18 wherein the nucleic acid is RNA.

21. The method of claim 1 wherein the signal generating moiety is an oligonucleotide.

22. The method of claim 1 wherein the signal generating moiety is a homopolynucleotide.

23. The method of claim 4 wherein the biotin is capable of binding to a conjugate containing an enzyme.

24. The method of claim 23 wherein the enzyme is a peroxidase.

25. The method of claim 23 wherein the enzyme is alkaline phosphatase.

26. The method of claim 1 wherein the labels on the signal generating moiety are fluorophores.

27. The method of claim 1 wherein the labels on the signal generating moiety are chemiluminescent.

28. The method of claim 1 wherein the labels on the signal generating moiety are catalysts.

29. The method of claim 1 wherein the labels on the signal generating moiety are dyes.

30. The method of claim 1 wherein the labels on the signal generating moiety are metal.

31. The method of claim 30 wherein the labels are colloidal gold.

32. A labeled nucleotide probe comprising:
   a) a first target recognition moiety having a first specific end sequence of at least about 4 nucleotide bases;
   b) a second signal generating moiety having multiple labels attached thereto and having a second specific end sequence of at least about 4 nucleotide bases; and
   c) a bridging complement comprising a nucleotide sequence of about 8–25 nucleotides;
   said specific end sequences of said moieties having termini aligned and chemically attached so that a 3' terminus of one of said moieties is aligned with a 5' terminus of the other, forming a 3'–5' sugar-phosphate chemical bond; and
   said bridging complement hybridized at least in part to said specific end sequence only of each of said first moiety and said second moiety.

\* \* \* \* \*